United States Patent
Simon

(10) Patent No.: US 7,543,718 B2
(45) Date of Patent: Jun. 9, 2009

(54) SYSTEM AND METHOD FOR STORING AND DISPENSING MEDICATION

(76) Inventor: Morris Simon, 8 Otis Pl., Boston, MA (US) 02108

( * ) Notice: Subject to any disclaimer, the term of this patent is extended or adjusted under 35 U.S.C. 154(b) by 345 days.

(21) Appl. No.: 11/085,235

(22) Filed: Mar. 22, 2005

(65) Prior Publication Data

US 2005/0218152 A1    Oct. 6, 2005

Related U.S. Application Data

(60) Provisional application No. 60/554,917, filed on Mar. 22, 2004, provisional application No. 60/646,995, filed on Jan. 27, 2005.

(51) Int. Cl.
*B65G 59/00* (2006.01)
*B65H 3/00* (2006.01)
*G07F 11/00* (2006.01)
*G07F 11/06* (2006.01)
*B65D 85/28* (2006.01)
*A47F 1/00* (2006.01)
*B65G 15/00* (2006.01)
*B65G 17/00* (2006.01)
*B65G 19/00* (2006.01)

(52) U.S. Cl. ............................ 221/13; 221/90; 206/380; 312/97.1

(58) Field of Classification Search ................ 221/122, 221/9, 13, 76, 79, 81, 92, 119, 121, 242, 221/241, 203, 215, 230, 113, 90; 220/215, 220/230; 700/242; 206/380; 312/97.1
See application file for complete search history.

(56) References Cited

U.S. PATENT DOCUMENTS

| | | | | |
|---|---|---|---|---|
| 2,953,242 A | | 9/1960 | Shaw | |
| 3,146,043 A | * | 8/1964 | Johnson et al. | 312/97.1 |
| 4,049,330 A | * | 9/1977 | Schlapp | 312/186 |
| 4,124,143 A | | 11/1978 | Thomas | |
| 4,203,518 A | * | 5/1980 | Current | 206/380 |
| 4,298,125 A | * | 11/1981 | Berghahn et al. | 206/531 |
| 4,317,604 A | * | 3/1982 | Krakauer | 312/97.1 |
| 4,334,617 A | * | 6/1982 | Rossmo | 206/534 |

(Continued)

FOREIGN PATENT DOCUMENTS

DE    3726257 A1    2/1989

OTHER PUBLICATIONS

Simon, Josephine, International Search Report for PCT/US05/09351, filed Mar. 22, 2005.

*Primary Examiner*—Gene Crawford
*Assistant Examiner*—Rakesh Kumar
(74) *Attorney, Agent, or Firm*—Nixon Peabody LLP; Jeffrey L. Costellia

(57) ABSTRACT

A customizable container is used with a method of filling, storing, and dispensing medication. The method employs a medication database and analyzes medication storage requirements to determine a customized container size and configuration for an individual pill-user. Container preparation instructions are generated to computer-tailor the customized container based upon the determined needs of the individual pill-user. A pharmacist uses the container preparation instructions to organize medications in the proper dosage administration sequence in separate reconfigurable compartments of the pill pack container. The pill pack container is individually customized for each individual pill taker to organize, store, and dispense correctly a supply of pills of multiple types, sizes, and shapes for a predetermined time period.

5 Claims, 11 Drawing Sheets

U.S. PATENT DOCUMENTS

| | | | |
|---|---|---|---|
| 4,453,326 A * | 6/1984 | Hoffman et al. | 40/377 |
| 4,572,376 A | 2/1986 | Wrennall | |
| 4,927,051 A * | 5/1990 | Falk et al. | 221/12 |
| 5,014,851 A | 5/1991 | Wick | |
| 5,048,717 A * | 9/1991 | Falk et al. | 221/2 |
| 5,154,296 A * | 10/1992 | Cutler | 206/534 |
| 5,174,451 A | 12/1992 | Niven | |
| 5,322,166 A | 6/1994 | Crowther | |
| 5,472,113 A | 12/1995 | Shaw | |
| 5,524,775 A * | 6/1996 | Kaine | 211/131.1 |
| 5,762,199 A | 6/1998 | Aguilera | |
| 5,887,719 A | 3/1999 | Edwards | |
| 5,921,394 A | 7/1999 | Shroff | |
| 6,032,609 A | 3/2000 | Luoma | |
| 6,062,420 A | 5/2000 | Krouwel et al. | |
| 6,068,158 A * | 5/2000 | Chabout | 221/113 |
| 6,126,010 A | 10/2000 | Kogen | |
| 6,550,618 B2 | 4/2003 | Peterson | |
| 6,601,729 B1 | 8/2003 | Papp | |
| 2003/0200726 A1 | 10/2003 | Rast | |
| 2004/0140242 A1 | 7/2004 | Davies | |
| 2004/0178112 A1 | 9/2004 | Snyder | |
| 2005/0029156 A1 | 2/2005 | Girzaitis | |

* cited by examiner

SYSTEM AND METHOD FOR STORING AND DISPENSING MEDICATION

CROSS-REFERENCE TO RELATED APPLICATIONS

This application claims benefit of priority to provisional application Ser. No. 60/554,917 filed on Mar. 22, 2004, and to provisional application Ser. No. 60/646,995 filed on Jan. 27, 2005, the disclosures of these applications being incorporated herein by reference.

BACKGROUND OF THE INVENTION

1. Field of the Invention

The present invention relates to the field of medication dispensers. More particularly, the invention relates to systems and methods for storing, and dispensing medication using a dispenser with customizable compartments. The present invention further relates to the determining, stocking, and dispensing of medication using a method of analyzing medication storage requirements to select the configuration of the storage dispenser.

2. Description of the Related Art

Many people take a large number of pills every day. Medications are frequently prescribed by physicians. Vitamin or mineral supplements, and alternative "natural" therapies may also be recommended by friends or magazines, or selected from drugstore, supermarket, or health-food store shelves. Some people take only one or two pills per day, while others may take as many as twenty or more. The effects of medicine on the human body can be important and powerful, so the pills should always be taken exactly as directed.

Handling pills in the home can be very confusing, not only for an elderly, sick, or forgetful person, but even for knowledgeable and attentive individuals. Most medications are taken in the form of pills or capsules that vary widely in size, shape and color. Some containers hold just a few pills for a short period; others hold hundreds for long-term use. Generally, there is a separate container provided by the pharmacy for each type of pill. Pills are dispensed and sold in a broad range of glass, plastic or cardboard containers, separately packaged, and are sometimes difficult to open. Accompanying instructions for use may be complex and hard to read or understand.

In an attempt to eliminate the need for a consumer to store and select multiple containers daily, containers for multiple pills have been developed to permit pills to be dispensed over a specific period; generally for one day or one week. These conventional multiple-pill containers are usually of a fixed size. Known multiple-pill containers are designed to be filled manually by the consumer who must choose pills from the multiplicity of individual pill containers furnished by the pharmacy or other source, and the consumer must accurately sort and sequence these pills in the multiple-pill container. This is not only time consuming but is also subject to error.

People normally take their pills at home without supervision or assistance. Specific pills may need to be taken at different times of the day. People sometimes forget to take their pills, take the wrong number, or take them at the wrong time. They often cannot remember, or do not understand, why they are taking some pills. There may be unintended breaks in the treatment program. For example, if a patient forgets to get a new prescription and runs out of pills, an unintended break occurs while the patient refills the prescription. In addition, the high cost of some medications may make them unaffordable, so fewer pills may be taken by the consumer than required, or the medications may be completely omitted from the treatment regimen.

Unrecognized adverse effects may occur as a result of taking too few or too many pills. Poor compliance with this important aspect of medical treatment can defeat the intended purpose of the treatment program. The effect of the medications may be significantly reduced or excessively exaggerated, and an illness may be prolonged or worsened. Furthermore, medical incompatibility between certain pill combinations can cause serious symptoms that may remain unexplained, or may be misdiagnosed and treated improperly. In some cases, dangerous medical complications can result. Physicians are concerned about the significant risks associated with poor compliance as well as the potentially serious results of drug incompatibility. Health-care providers have become alarmed by the magnitude of these problems nationally. People clearly need help to deal with this very difficult home health care situation.

What is needed is a system and a method for accurately filling, storing, and dispensing medication to provide health care consumers, an effective, and efficient, manner of complying with their treatment regimen.

SUMMARY OF THE INVENTION

The present invention relates to a system and method for storing, and dispensing medication using a container with customizable compartments. The present invention provides a powerful and elegant manner of determining, stocking, and dispensing medication using a method of analyzing medication storage requirements to optimize the configuration of the storage apparatus. The storage system of the present invention combines computer technology with a unique, reconfigurable pill pack container that is computer-tailored to the needs of each individual pill-user.

The present invention provides a computer-based method for providing a pharmacy with a list of the multiple pill types taken by an individual over a predetermined time period, and method for organizing these medications in proper sequence in separate, reconfigurable compartments of a pill pack container. The pill pack container is individually customized to correctly organize, store, and dispense, a pill-user's supply of pills of multiple types, sizes, and shapes. A computer program includes the size and shape of the different pills to be taken during the time period, and the information is used to develop a computer-generated preparation instructions for the pill pack container specifying the configuration and size of each pill compartment and the exit port size for each compartment. The reconfigurable pill pack container is subdivided into a number of separate large storage compartments. Each large storage compartment may be subdivided into smaller compartments by removable divider walls. Divider walls of different shapes and sizes allow customized configurations with different compartment sizes and geometries.

The present invention extends the functionality of current methods and systems used to dispense medication by creating a system and method for storing and dispensing medication using a container with customizable compartments. As explained below, the medication storage requirements are analyzed to optimize the configuration of the storage apparatus. Thus, in one embodiment, the storage system of the present invention combines computer technology with a reconfigurable pill pack container that is computer-customized to the needs of each individual pill-user. The system and method of the present invention has many advantages over prior medication systems, because the single pill pack container is configured, filled, and dispensed by a trained pharmacist and provides a customized, single container that organizes a patient's medication requirements for accurate administration. The likelihood of dosage errors is reduced, and medication records may be accurately tracked. The present invention can significantly reduce medication errors and dispensing costs by providing a customized medication regimen which can be administered by a convenient and reliable system based upon individual patient's pill requirements.

The present invention addresses serious deficiencies of prior systems by introducing two reforms into the current pill management systems, namely the use of a new compact plastic pill pack container, and optionally, having a pharmacist configure and fill the individually customized pill pack. The novel pill pack simplifies the organization, storage, and dispensing of all the pills taken at home by each pill-user. The pill pack container may be implemented in a range of different sizes, and be further adjustable to fit each user's precise needs, which vary widely from person to person.

In one preferred embodiment, the pharmacist, already the traditional supplier of the pills, is in charge of the pill pack system of the present invention. The pharmacist uses a pill pack computer program in accordance with one aspect of the present invention to enter and process an individual's medication data, customize the pill pack container, print labels, fill the pill pack container, and facilitate periodic refills. The traditional face of the pharmacist has changed over the years, and as such, in all embodiments of the present invention, the pharmacist may be anyone engaged in the art, practice, or profession of preparing, preserving, compounding, or dispensing medical drugs. The pharmacist may be around the corner, across the country, or any location, and may be contacted in person, in telephonic communication, or over any communication network, such as the Internet, for example, to configure and fill a pill pack container for a particular pill-user.

The pharmacist is the most natural, logical, and best-trained health professional to take charge of this important, but greatly neglected aspect of health care. The local pharmacy is already the primary source of most medications. The pharmacist is also comfortable with computerized medical information systems, patient databases, and label printing. The preferred implementation of the present invention may be readily managed by pharmacists since the present invention integrates and expands the pharmacist's current functions. The method of the present invention enables the pharmacist to consolidate an entire medication regimen with a single pill-user transaction, and uses a compact customized container to store and dispense all the pills. The pill pack computer software and pill pack container provide a direct bridge connecting the pharmacist to the pill-users.

BRIEF DESCRIPTION OF THE DRAWINGS

The above-mentioned and other features of this invention, and the manner of attaining them, will become more apparent, and the invention itself will be better understood, by reference to the following description of embodiments of the invention taken in conjunction with the accompanying figures where.

DETAILED DESCRIPTION OF THE INVENTION

The invention is described in detail with particular reference to certain preferred embodiments, but the invention is not limited to such embodiments. It will be apparent to those of skill in the art that various features, variations, and modifications can be included or excluded.

Figure 1:
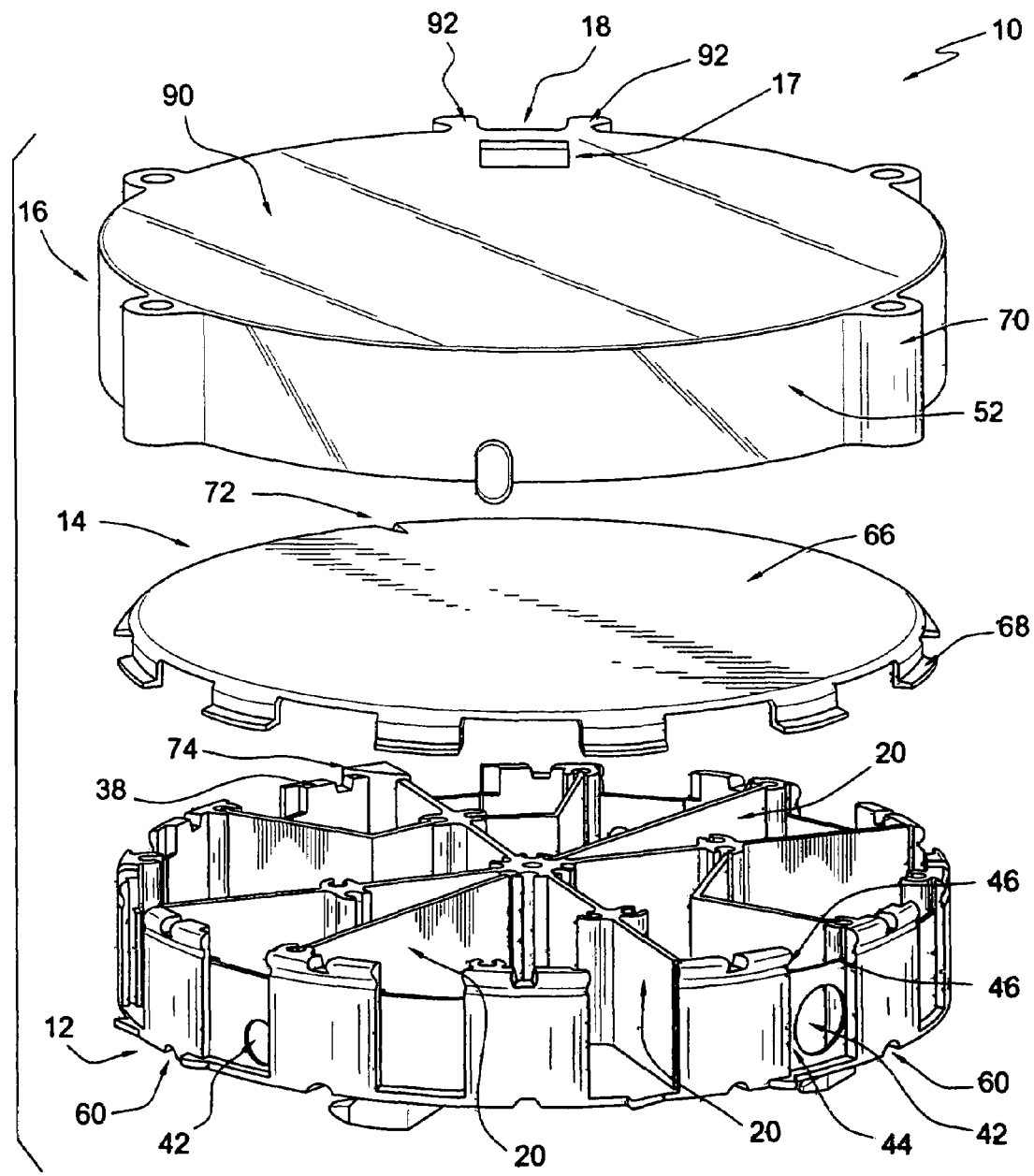
FIG. 1 illustrates an exploded top perspective view of the reconfigurable pill pack container in accordance with one embodiment of the present invention.
Figure 2:
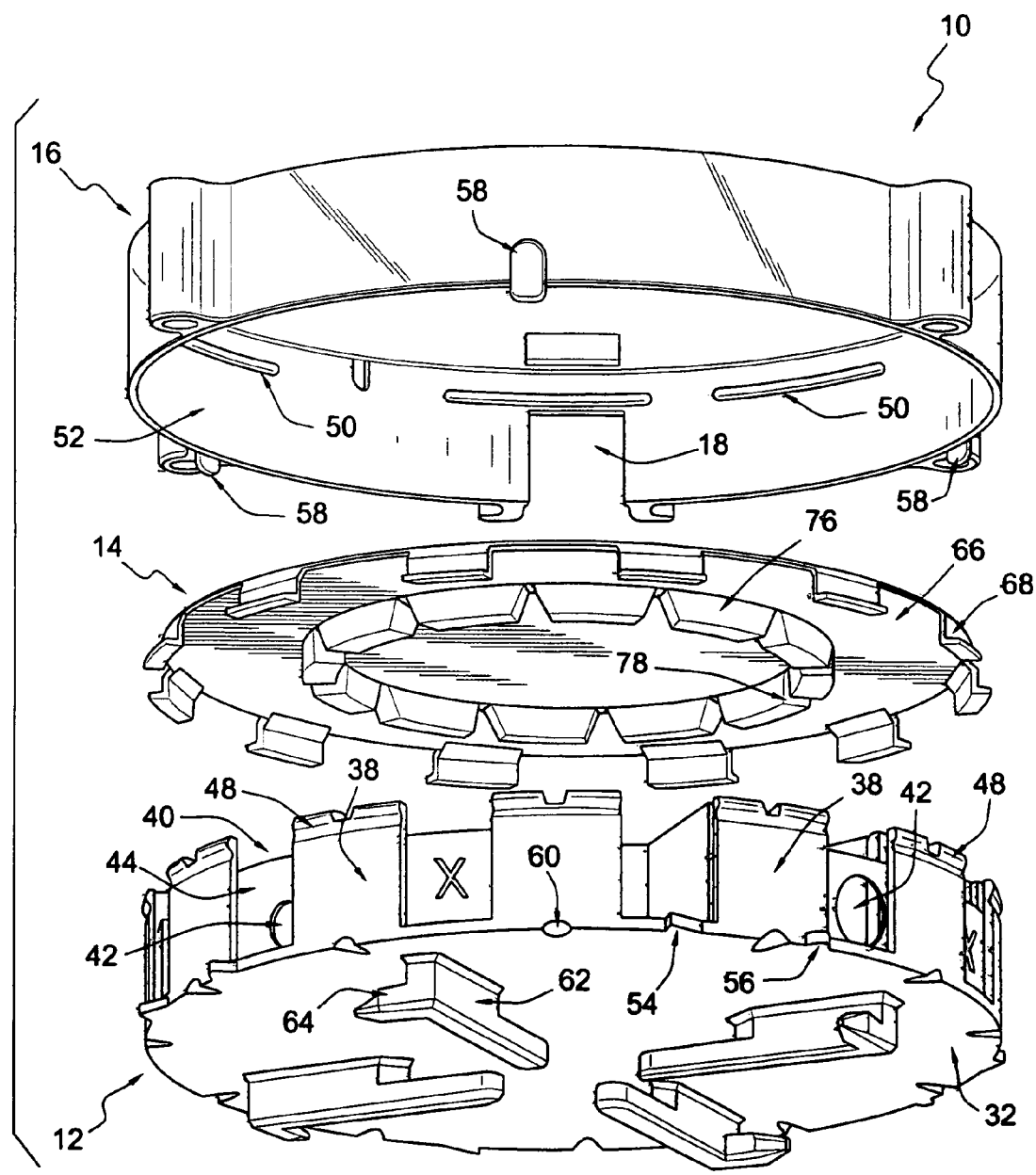
FIG. 2 illustrates an exploded bottom perspective view of the reconfigurable pill pack container in accordance with the embodiment of the present invention as shown in FIG. 1.

FIG. 1 and FIG. 2 illustrate the pill pack container in accordance with one embodiment of the present invention. The pill pack container is indicated generally at 10 and in the illustrated embodiment, is a circular container, organizer, and dispenser, which can be subdivided into a variable number of separate storage compartments. The pill pack container is compact, lightweight and handheld, and can be implemented in different sizes to store a supply of all the pills taken by an individual for a predetermined length of time, for example, one month.

A preferred embodiment of the pill pack container 10 of the present invention comprises three parts. These parts include a rotatable tray 12 that is subdivided by a series of radial walls 20 into separate variable-sized storage compartments that hold the pills; a plastic lid 14 that fits on top of the tray 12; and a cover 16 that encloses the combined tray 12 and lid 14. The cover 16 is implemented to be transparent in the illustrated embodiment, and to have a single dispensing opening 18 (also shown in FIG. 2) formed in its peripheral wall 52. The three parts will be described separately, although the tray 12 and lid 14 function as a single unit that is rotatable relative to the cover 16 to dispense pills from each open compartment port-hole opening 42 in turn. As such, the lid 14 disposed between the tray 12 and cover 16 may be combined with cover 16 to form a two-piece container. In either case, the pill pack container 10 of the present invention employs a preparation diagram and other labels to capitalize upon the computer-implemented method of filling the pill pack container as described in further detail below. In addition, several pill pack sizes, and some useful accessories are also described below.

Figure 3:
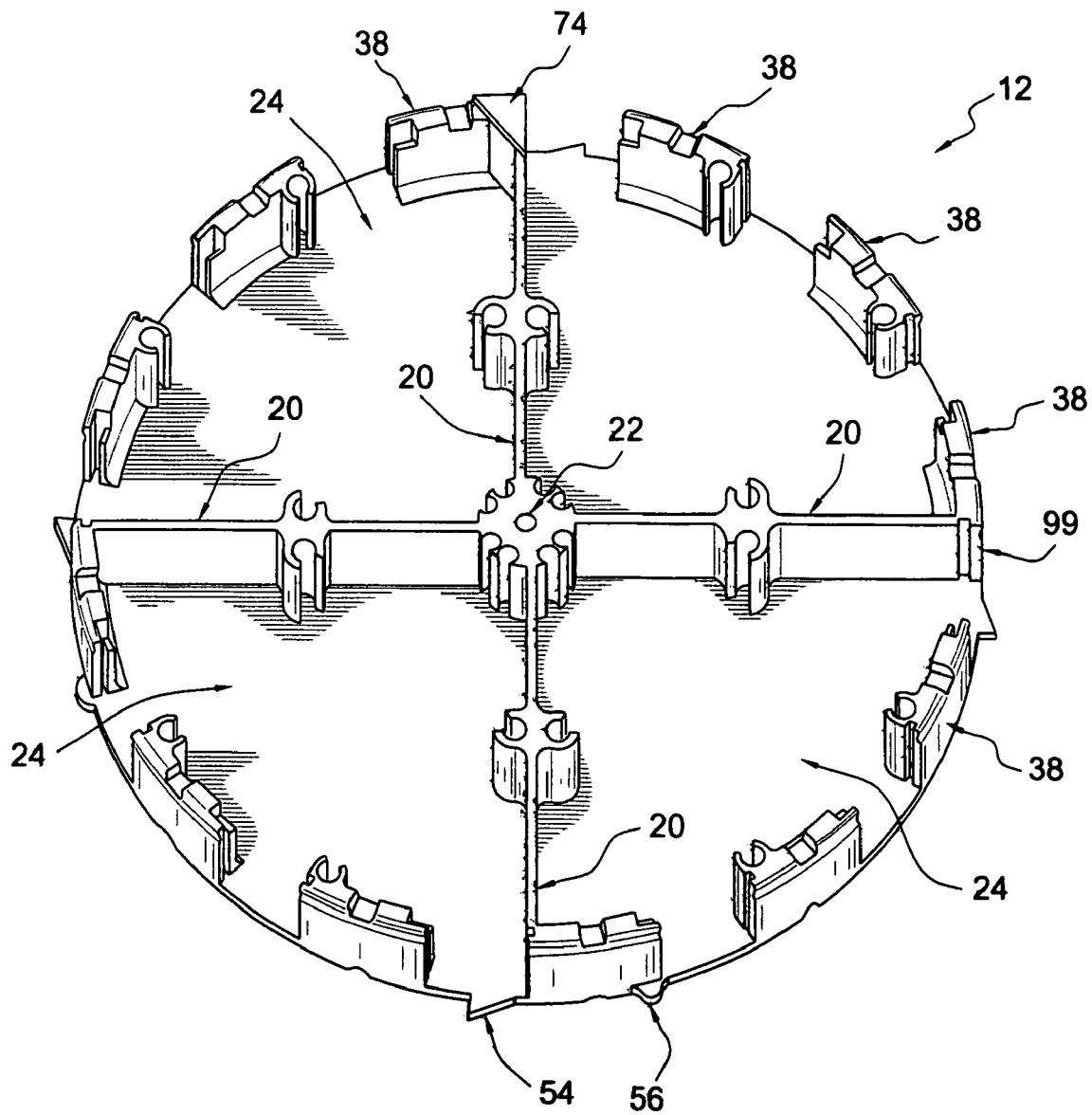
FIG. 3 shows a top perspective view of the tray provided with radial walls for the pill pack container of FIG. 1.

As also shown in FIG. 3, the tray 12 is subdivided by a number of radial walls 20 that radiate from a center post 22 to a perimeter rim 99 comprised of separate upright tray rim segments 38. The radial walls 20 and perimeter rim 99 form a few large compartments 24 (four large compartments), each having a capacity of approximately 60 ml in the illustrated embodiment. The pill pack containers can be implemented with various sizes having one to seven such large compartments, and therefore may be identified by their size numbers 1, 2, 3, 4, 5, 6, and 7.

Figure 4:
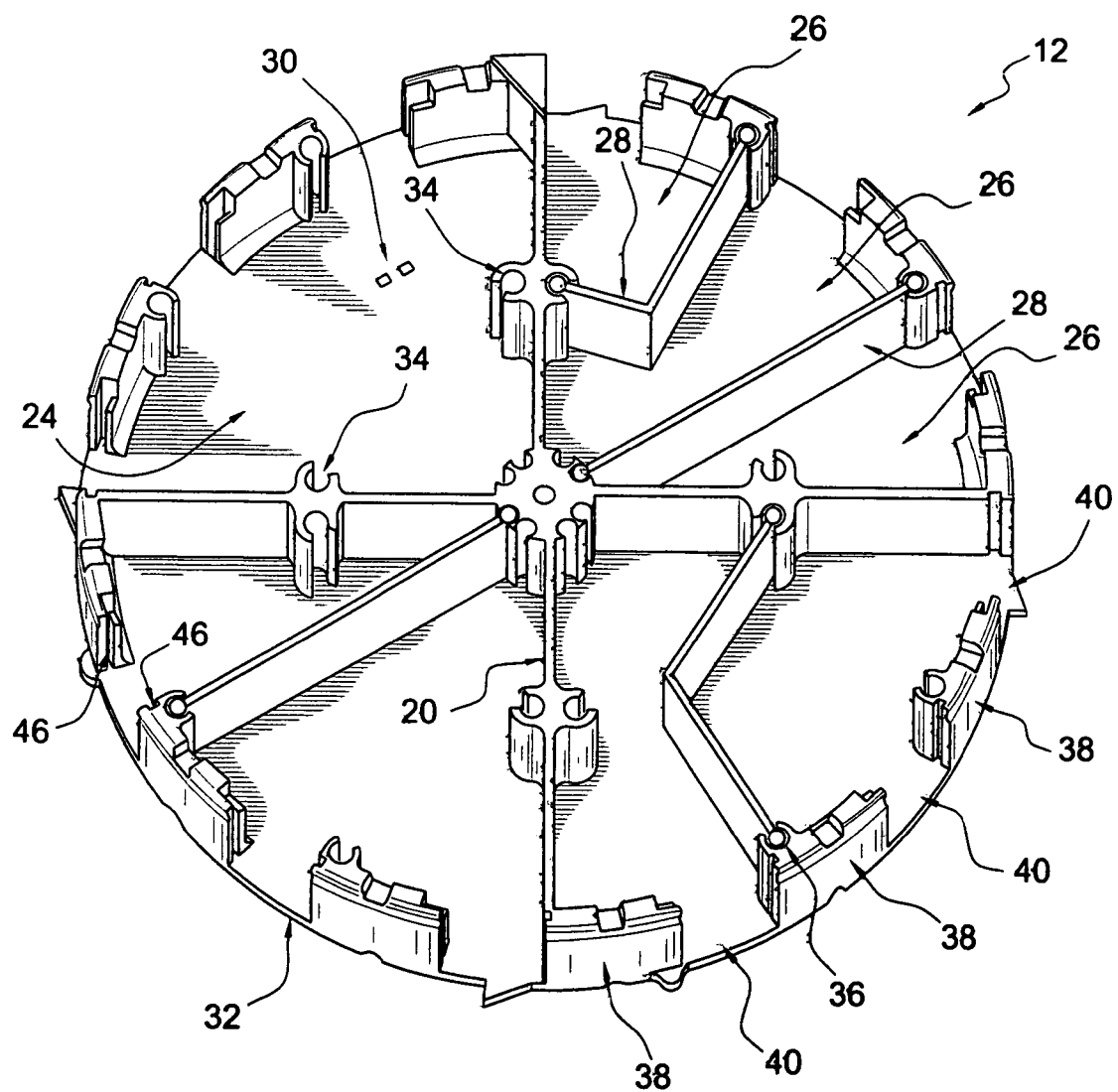
FIG. 4 illustrates a top perspective view of the tray provided with removable divider walls for the pill pack container in accordance with one embodiment of the present invention.

As further shown in FIG. 4, each 60 ml compartment may be further subdivided into smaller pill compartments 26 by using removable divider walls 28. The divider walls may be implemented in various shapes including Straight divider walls. In accordance with the preferred embodiment, the divider walls may also be non-planar in shape including Standard-L shaped, Reverse-L shaped, Straight, or Chevron-shaped. These differently shaped removable walls make it possible to subdivide the large compartments 24 to create smaller compartments 26, that measure, for example, 45 ml, 40 ml, 30 ml, 25 ml, 20 ml, or 15 ml, in various combinations for pills of different sizes. The 15 ml compartment can hold about 35 fairly small pills, more than a typical one-month's supply of medication. The larger-sized pill compartments are used for increasingly larger pills. The non-planar removable divider walls 28 may be used to increase the number of compartments in the pill pack container 10. These non-planar removable divider walls are positioned into spaced, vertically extending surface projections 30 formed in the tray bottom wall 32 of the tray 12. As best shown in FIG. 4, vertical slots 34 and 36 formed in the radial tray walls 20 and in a tray rim segment 38, respectively, extend upwardly from the tray bottom wall 32. The tray rim segment 38 defines three tray port openings 40 for each large compartment 24 in the illustrated embodiment. As also shown in FIG. 1, the pill pack container 10 is further provided with port inserts 44, which slides into opposed vertical slots 46 formed in the tray rim segment 38 on either side of each tray port opening 40. The port inserts 44 may be a closed, planar insert, or be provided with a porthole opening 42 thereon, the port hole opening being sized as described in detail below.

The tray port openings 40 may be 15 mm wide, and located between each pair of tray rim segments 38. Any tray port opening 40 can be closed completely, or may be reduced in size by inserting a port insert 44 prescribed in a preparation instructions that are computer-generated for the individual pill-user. Three port insert options may be made available in one implementation. The port insert options may include Closed (X), Small (7 mm diameter opening), or Medium (11 mm diameter opening). A Large (15 mm square) porthole opening simply requires that no insert be placed in a tray port opening 40, while unused tray port openings 40 to be closed off receives a Closed (X) port insert. The size of the porthole corresponds to the size and shape of the pills stored in that compartment.

In using the pill pack container 10, preparation instructions may be computer-generated at the pharmacy for each individual pill-user. Preferably, the preparation instructions schematically illustrate the specified tray in actual size. This preparation diagram shows the location and type of each non-planar removable divider wall 28, and the correct port insert 44 required, for each pill compartment 26. The pill pack container 10 is received from the manufacturer with a set of removable divider walls 28 pre-installed. To comply with the preparation diagram, the pharmacist removes or rearranges some of the divider walls, and other divider walls may be added to configure a pill pack container in accordance with the preparation diagram. Additionally, the pharmacist inserts the proper port inserts 44 as instructed. Once the port inserts are set in place and the divider walls are correctly positioned as prescribed, the preparation diagram has fulfilled its purpose and may be discarded.

FIG. 2 illustrates an exploded bottom perspective view of the reconfigurable pill pack container 10. As shown in FIG. 2, there is a shallow tray groove 48 formed in the tray rim segments 38 just below the upper edges thereof. The tray groove 48 extends around the tray rim segments 38, just above the level of the port inserts 44. A ring of inwardly projecting rotation ridge segments 50 is provided inside the peripheral wall 52 of the cover 16. The ring of rotation ridge segments engage the tray groove 48 to secure the cover 16 to the tray 12, but still allow the tray 12 to be rotated relative to the cover 16.

As shown most clearly in FIG. 3, along its lower edge, the tray 12 has a series of paired wedge and bump projections 54 and 56 respectively, which extend radially outwardly from the tray 12. As the tray 12 is manually rotated under the cover 16, a paired wedge 54 and bump 56 engage short cover legs 58 which extend downwardly from the cover's peripheral wall 52. The paired wedge and bump projections 54 and 56, and the cover legs 58 are positioned to engage when the porthole openings 42 of the tray are aligned with the dispensing opening 18 of the cover 16. This produces a positive stop engagement and a click-stop sensation as each porthole opening 42 is aligned with the dispensing opening 18 of the cover 16.

Alternatively, the tray groove 48 and the rotation ridge segments 50 need not be provided. Instead, other methods may be used to secure the cover 16 to the tray 12. For example, cover 16 can be removably secured to the tray 12 by modifying the cover legs 58 to include two small holes near the tip of each of the cover legs 58 closely adjacent to the tip thereof. With the cover 16 in place on the tray 12, a small removable L-shaped wire-clip stud may be inserted through the two holes in each cover leg 58 so that while one section presses against the rim of the cover 16, the other extends under the edge of the tray 12. The clips thus secure the cover 16 to the tray 12, but permit the tray 12 to be rotated relative to the cover 16. The clips may be removed from the cover 16 manually in order to lift the cover 16 off the tray 12 for a refill or a tray modification. The clips would eliminate the need for the rotation ridge segments 50 on the rim of the cover 16, the tray groove 48, and an optional baseplate which can otherwise be used to remove the cover. Of course, the above-described implementations are merely provided as examples and any appropriate mechanism may be used.

As also shown in FIG. 2, the lower edge of the tray rim segments 38 also has a small notch 60 at the lower edge of each compartment. These notches 60 help to grip an optional rubber lock-loop (not shown) that can be used to tie the cover 16 and tray 12 tightly together for security purposes where there are young children, or for travel, or when the medication must otherwise be secured.

As shown in FIG. 2, four downwardly projecting tray rotation bars 62 are provided under the tray 12 on the bottom wall 32 to help the user's hand in rotating the tray 12 relative to the cover 16. The rotation bars of the illustrated embodiment also have undercut outer tips 64, which can secure the pill pack container onto an optional baseplate (not shown), which may be used to safely disengage the cover 16 from the tray 12 to facilitate re-filling.

As shown in FIG. 1 and FIG. 2, the lid 14 is a disc that fits on top of the tray 12. The lid 14 has a lid topwall 66 from which downwardly spaced lid sidewall segments 68 extend. These lid sidewall segments 68 fit partially over the tray port opening 40. Many of the tray port openings 40 will receive port inserts 44 to close the tray port opening 40, or reduce the size of the opening. Lid sidewall segments 68 provide rigidity support for port inserts 44 that may be fitted into tray port openings 40.

As shown in FIG. 1, the lid 14 is correctly aligned with the tray 12 when a triangular cut-out 72 on the edge of the lid 14 fits over a matching triangular projection 74 formed by a corner of a radial wall 20 and a tray rim segment 38 on the outer edge of the rim perimeter 99. The triangular projection 74 and its position relative to the entire tray 12 is best shown in FIG. 3. Returning to FIG. 2, a stabilizer ring 76 projects downwardly from the lid topwall 66 and is provided with spaced slots 78 which receive and hold the non-planar removable divider walls 28 securely in their assigned positions within the tray 12 when the lid 14 is engaged with the tray 12.

Figure 5:
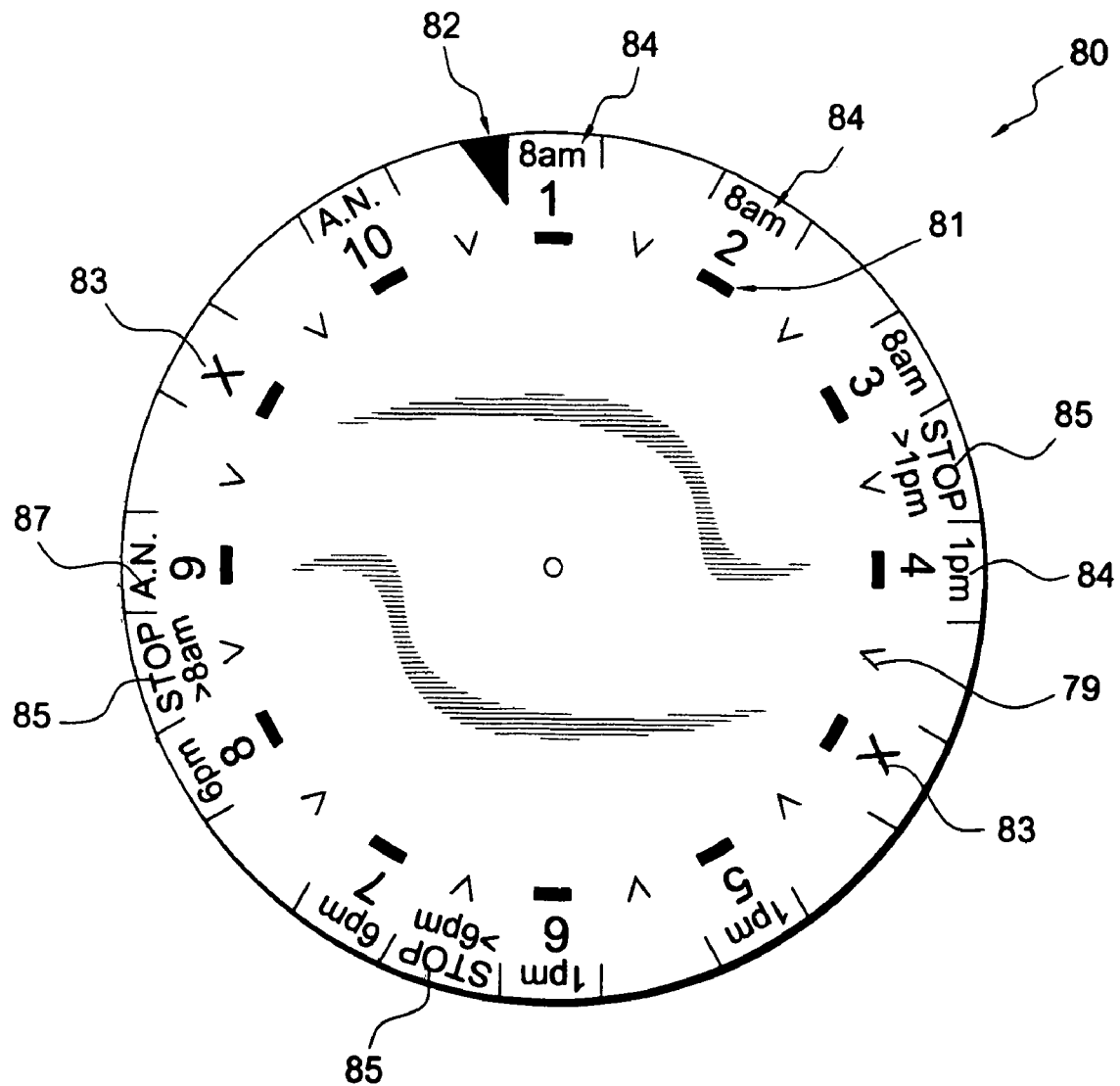
FIG. 5 is a top view showing the computer-generated lid label for the cover of the pill pack container in accordance with one embodiment of the present invention.
Figure 6:
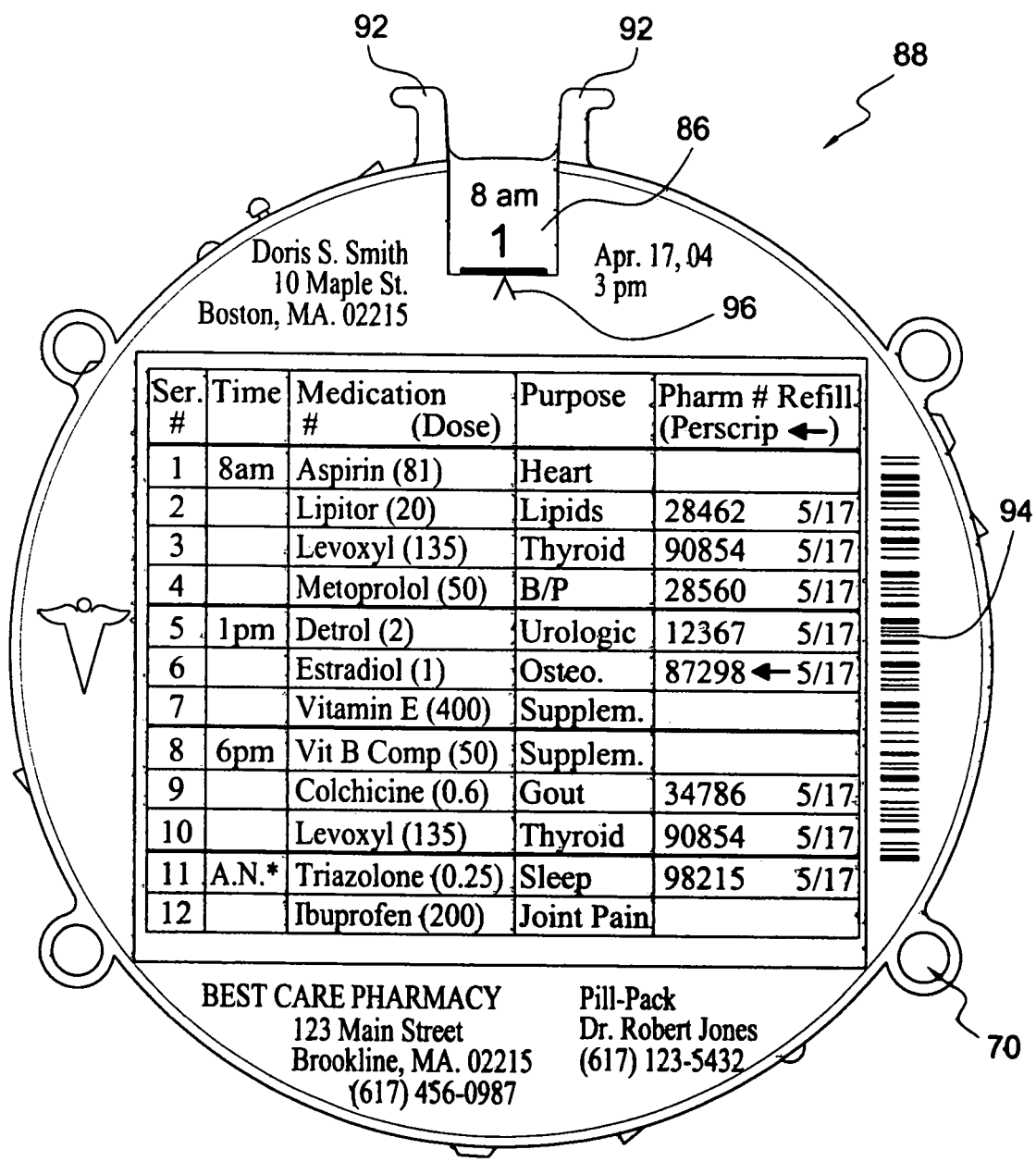
FIG. 6 is a top view showing the computer-generated cover label for the pill pack container in accordance with one embodiment of the present invention.

As shown in FIG. 5, a lid label 80 is printed for each pill-user and is attached onto the lid 14 by double-stick adhesive tabs (not shown) or other appropriate adhesive so that the printed triangle 82 is positioned over the triangular cut-out 72 on the edge of the lid 14. The lid label 80 has a series of preprinted 15 mm window spaces 84 around its perimeter, one for each potential radial compartment of the tray 12. Each window space 84 will be displayed to the pill-user in turn in the small window 86 at the top of a cover label 88 as porthole opening 42 rotates into the dispensing opening 18 as shown in FIG. 6. Inside each window space 84, the computer prints key features of that compartment. For example, if the port is open and pills can be dispensed, the window space 84 displays the compartment's series number and the time to take the pill. In the example configuration of FIG. 6, series number "1" is shown, and the time to take the pill is indicated as "8 am" If the pill can be taken any time, that is, as needed, its series number and "A.N." appear as shown by reference numeral 87. If the port is closed, an X appears in its box 83. In addition, a red "STOP" warning signal 85 appears in the space between the last box of any particular time slot and the first box of the next time slot. The time for the next lot of pills is also indicated.

In the embodiment shown in FIG. 1, the cover 16 has a transparent cover topwall 90 and peripheral wall 52. The cover 16 is more flexible than the tray 12. Peripheral wall 52 has a single dispensing opening 18 at the top, and is provided with side rails 92 that may be used to attach certain optional accessories. The dispensing opening is substantially square in shape in the illustrated embodiment and may be sized according to the capacity of the pill pack container, 15 mm for example.

Referring also to FIG. 2, the cover 16 fits snugly over the lid 14 and tray 12. However, the lower edge of the peripheral wall 52 stops just above the wedges 54 and bumps 56 on the lower edge of the tray 12. Three cover legs 58, which are evenly spaced in the illustrated embodiment, extend downward from the edge of the cover's peripheral wall 52. As the tray 12 is rotated, a wedge 54 lifts one cover leg 58 outward until it drops with a "click" over the apex of the wedge 54. Substantially simultaneously, a paired bump 56 engages one of the other cover legs 58 to "stop" the rotation by increasing resistance to relative rotation. Wedges 54 and bumps 56 are positioned to work in pairs to "click-stop" the rotation as each porthole opening 42 arrives in the dispensing opening 18 of the cover 16, i.e. the porthole opening 42 is aligned with the dispensing opening 18. The positive stop engagement of the wedges 54 and bumps 56 provides a safe and efficient rotation and closure method. A slightly increased rotation force can overcome the "stop" bump 56 and allow the rotation to continue to the next compartment wedge 54. Thus, each tray port opening 40 click-stops in turn as it arrives in the cover opening 18. If the compartment porthole opening 42 is open, that is, aligned with the dispensing opening 18, its series number will be displayed in the window 86 at the top of the cover label 88 shown in FIG. 6, and pills may be dispensed. The wedges 54 also allow the tray 12 to be hand-rotated in one direction only, that is, in a clockwise direction in the illustrated embodiment.

Referring again to FIG. 1, four cylindrical tubes 70 are provided on the cover's peripheral wall 52 and may be used as a security mechanism to prevent dispensing of pills when the tray 12 is midway between two click stops. These tubes 70 line up with four of the tray notches 60 on the lower edge of the tray 12 when the tray 12 is midway between two click stops, and dispensing is prevented. In this position, that is between two click stops, the tubes 70 and notches 60 receive an optional rubber lock loop to further secure the pill pack container 10.

Referring again to FIG. 6, the cover label 88 of the illustrated embodiment is printed by the pharmacist for each pill-user. The cover label 88 is mounted under the transparent cover 16 by adhesive tabs (not shown) and can be aligned with the cover window marks 86. The cover label 88 displays a computer-generated chart, which lists all the pills in the pill pack container compartments in the order in which they are dispensed. Each listed pill has been assigned a series number in that order. As each open port reaches a positive stop engagement and click-stops when aligned with the cover opening 18, its matching series number on the lid label appears in the cut-out window at the top of the cover label. Pills can now be dispensed from that compartment port by moving and/or shaking the pill pack container. Between port click-stops, no pills can be dispensed. In addition, at click-stops where the port has been closed, an X appears in the window instead of a series number, and pills cannot be dispensed or spilled since no porthole opening is in place.

Each line of the cover label 88 of the illustrated implementation shows the pill's series number, the time the pill is taken, how many pills to take, the pill's name, dose and purpose. Optionally, an image of the pills may be also provided to allow visual confirmation by the pharmacist and/or the pill-user. For prescription pills, the cover label 88 also displays a pharmacy number, a refill date, and a warning arrow if a new prescription is needed. The cover label 88 is also dated. For refills, a bar code 94 is provided to allow the pharmacist to identify the pill pack container owner and review the current pill regimen on a computer monitor. Additional information may also be provided on cover label 88. For example, the names and phone numbers of the owner, the pharmacist, and the referring physician may also be provided on the cover label, or on an optional rear tray label.

The large differences in the numbers and sizes of pills can be addressed by providing several different sized pill pack containers that can be selected for use. The pill pack containers may be supplied in overlapping sizes numbered 1, 2, 3, 4, 5, 6, and 7. The smallest size may hold a minimum of 1 compartment up to a maximum of 3. The next size may hold from 2 compartments to 6, while the next size may hold 3 to 9 compartments, then 4 to 12, then 5 to 15, then 6 to 18, and finally 7 to 21. The pill pack container size is thus specified by the minimum number of large pill compartments. The sizes of the pill pack containers may be engraved under the tray, and also on each removable part. Of course, container diameter, label sizes, number of compartments, and location of cover side cylindrical tubes, wedges, and bumps vary with the pill pack container size.

The porthole and compartment sizes for each pill taken by an individual may be determined in any appropriate manner, for example, by the pill pack computer program discussed in detail below. The total size of all the individual's compartment combinations may also be indicated by the pill pack computer program, and preferably the next available pill pack container size is selected for that person. This pill pack container size and the required size of every compartment and porthole are clearly prescribed on each preparation diagram provided by the pill pack computer program, with every compartment wall illustrated to tailor the pill pack container structure for the specific needs of the user. Optionally, multiple pill packs may be preferred for larger numbers of pills. For example, one pill pack for morning medications, and another for evening medications. It also may prove useful to have one pill pack for short term medications, and another pill pack for long term pills.

Additional embodiments of the present invention may incorporate any number of supplementary features used to assist the configuration of the pill pack container. Additional features contemplated include, but are not limited to, a space-saving cradle provided for upright storage. Alternatively, the pill pack may be hung from a special wall fixture. Further, a security pin-lock may be mounted on the rim of the cover, and a child-proof lock-loop may be used for extra security. Other options may include a handle that can be attached to the cover for easier tray rotation. Also, a pill-refill tray may be used to refill each depleted compartment in turn. To assist in opening and closing the pill pack container, a baseplate and an opening lever may be used to help to pry the cover off the tray. An elastic loading band may also be used to seal the open portholes while refilling. A mesh pill-purse may gather a few pills at a time rather than one-by-one. A plastic 35-pill volume measuring cup may be used to check the needed compartment size. A transparent comparator gauge may be used to check compartment and porthole sizes. Optional wire clips may be inserted into the cover arms to link the cover to the tray, while a binder may be used to collect standardized medical information sheets. Multi-alarm watches that are available already may also optionally be integrated within the pill pack container to provide an audible alarm indicative of the time to take medication. These and additional accessories may be used to extend the efficacy of the method and system of the pill pack container of the present invention.

Figure 8A:
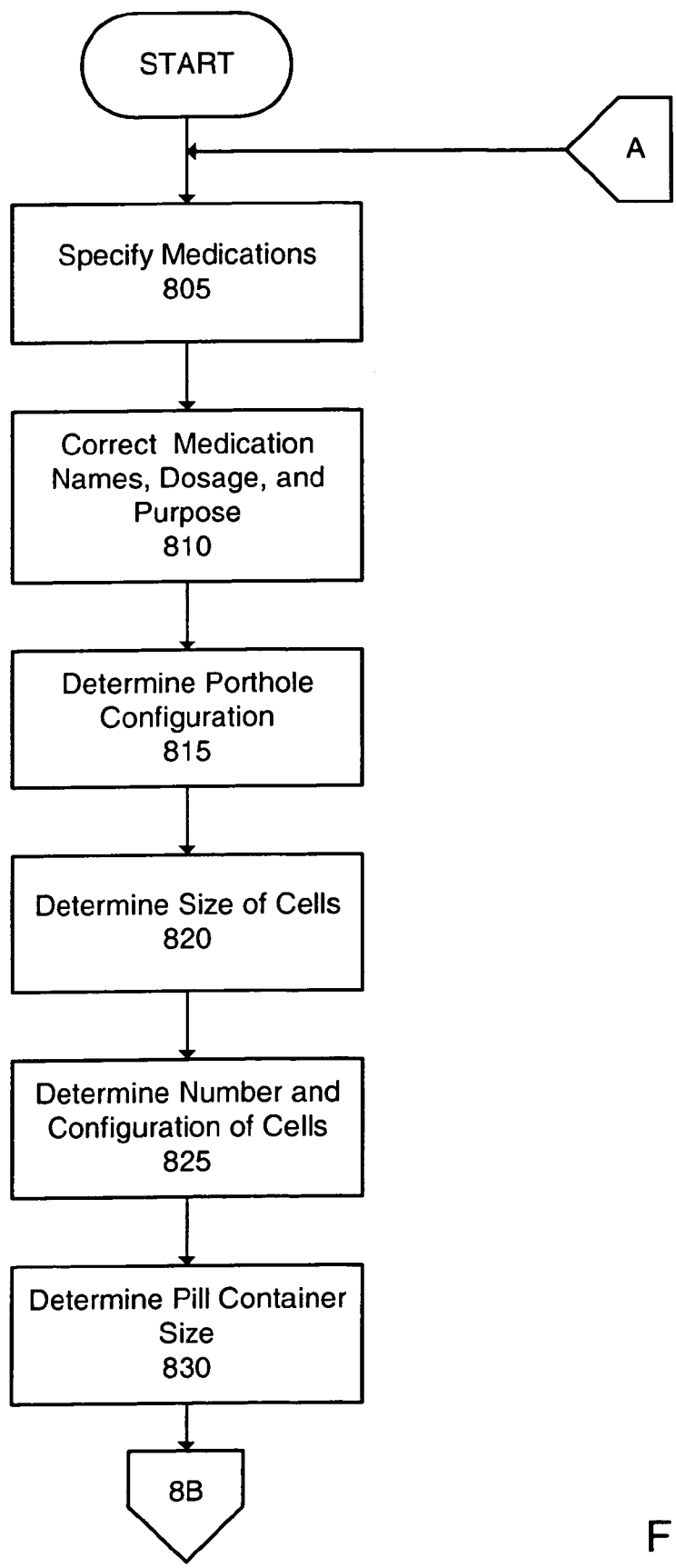
FIGS. 8A, 8B, and 8C are flow diagrams illustrating the computer-implemented method of configuring a pill pack container in accordance with the present invention.
Figure 8B:
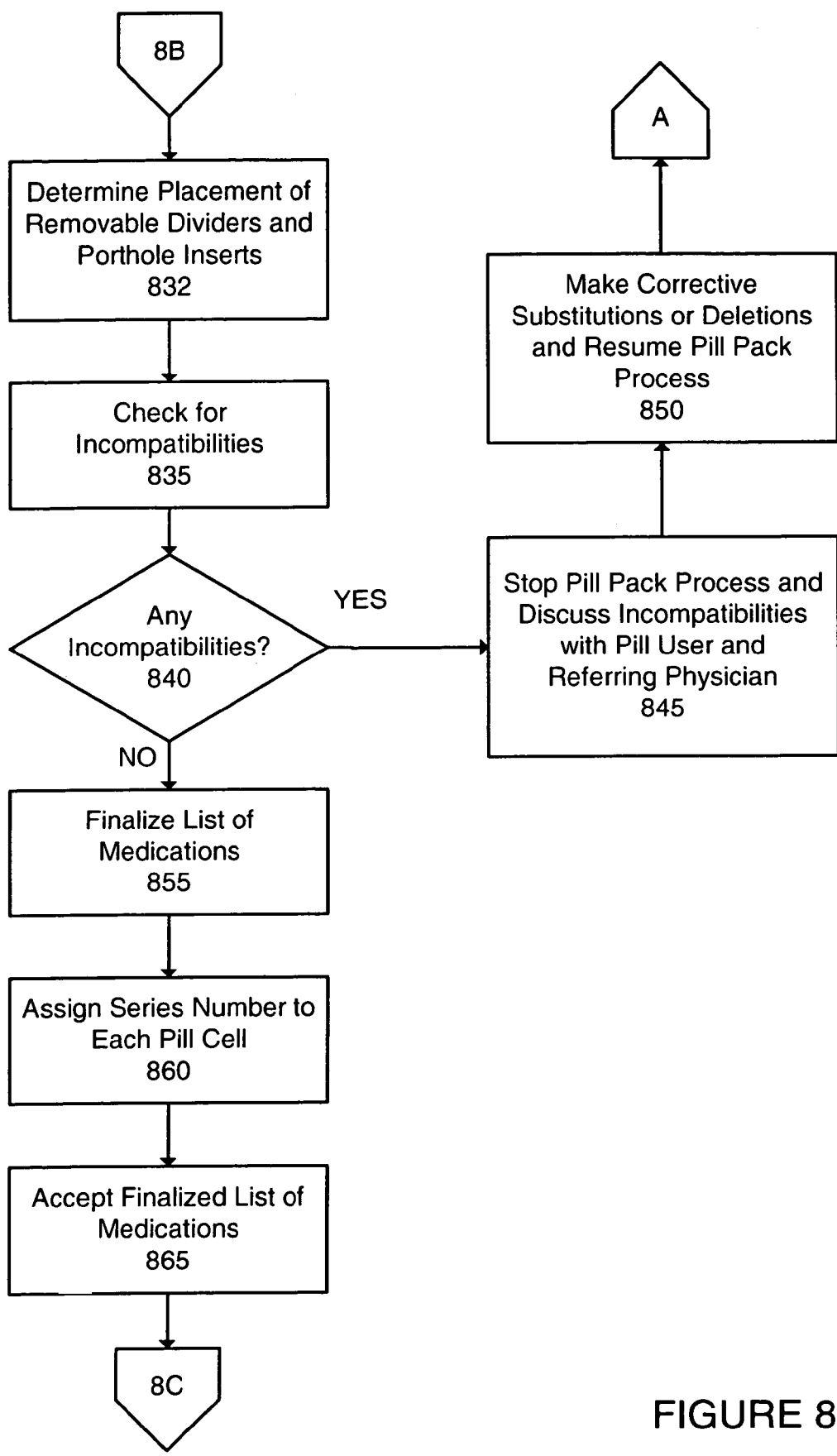
Figure 8C:
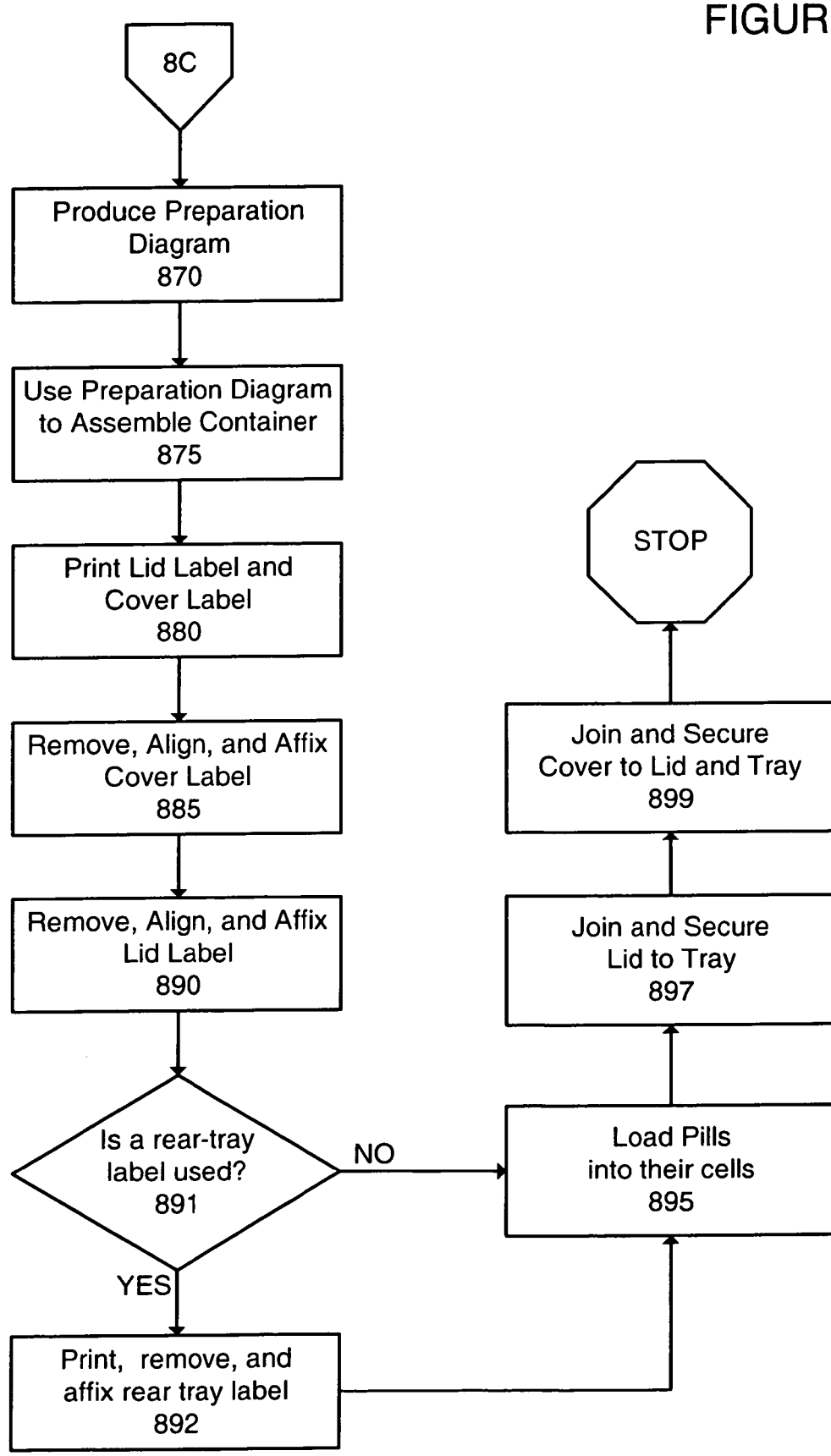

The process of configuring and filling the pill pack container of the present invention is illustrated by the flow chart of FIGS. 8A, 8B, and 8C. FIGS. 8A, 8B, and 8C illustrate the computer-implemented method of the present invention. As illustrated in step 805 of FIG. 8A, the process begins by specifying the medications used by a particular pill-user. The specific medications may be itemized by a number of methods including the patient completing a questionnaire, a physician writing a prescription, the pharmacist using the old medication bottles, or any other manner of specifying or listing the medications that a particular pill-user is taking. In a preferred embodiment, the medication list is specified by the patient completing a formatted questionnaire.

Figure 7:
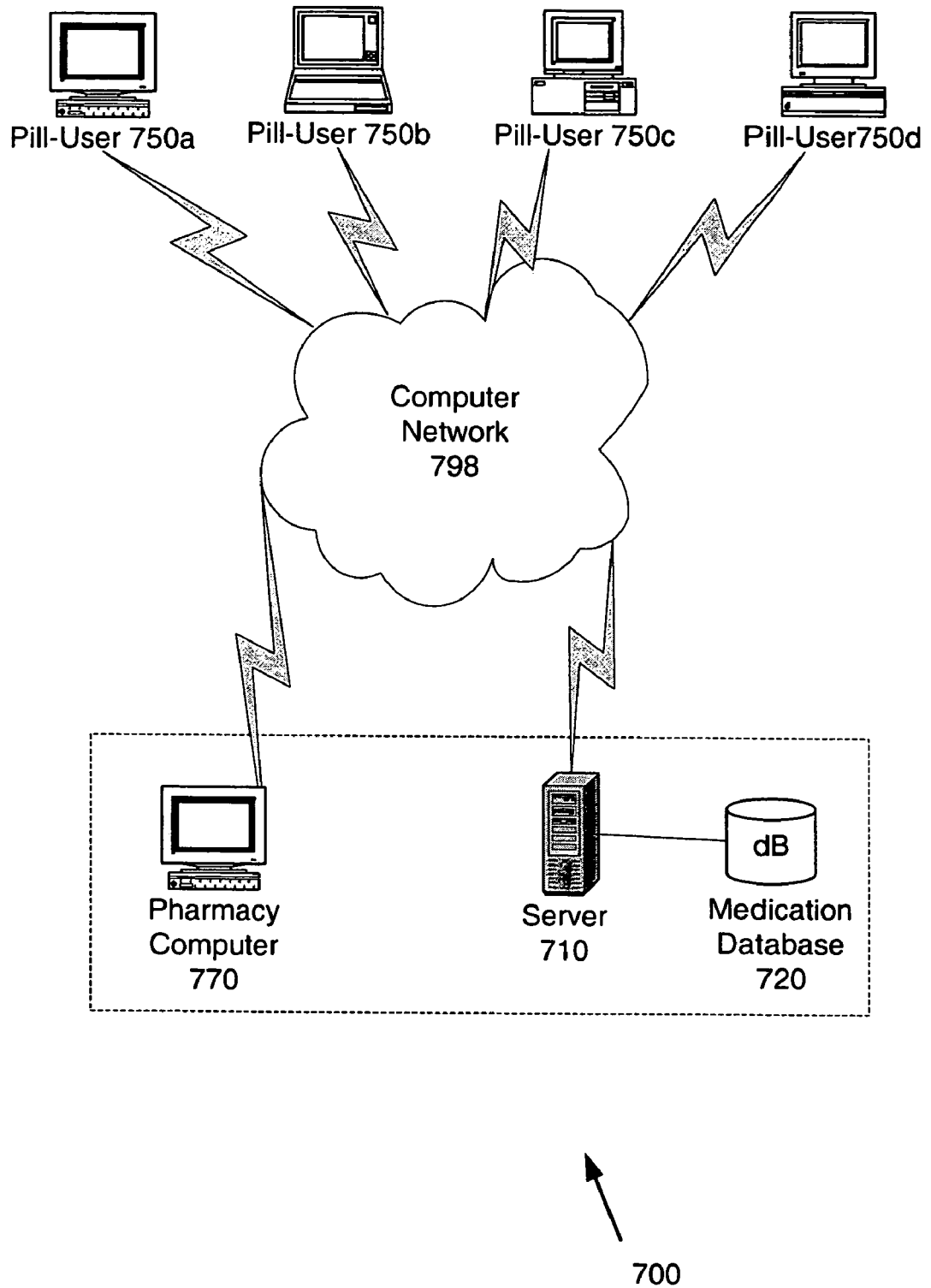
FIG. 7 illustrates an exemplary computer system used to perform the method of the present invention.

The blank form is supplied by the pharmacy on paper, or electronically on a computer network 798, as shown in FIG. 7 by a direct connection, a local area network, the Internet, or the like. The pharmacist may use computer system 700 to provide a blank form on an pharmacy computer 770 upon which a pill-user customer may complete. Similarly, the pharmacist may use the pharmacy computer 770 to send a blank form to a pill-user via computer network 798 for the pill-user to complete at home, or wherever the pill-user's computer 750a is located. Of course, multiple pill-users may also access and benefit from the method of the present invention by using other pill-user computers 750b, 750c, 750d, or any suitable input device that can be used to provide medication data to the pharmacy computer. The pharmacy computer 970 may also be located anywhere the prescription is to be filled, for example at a neighborhood pharmacy, a medication warehouse, or any other medication-filling entity. The pharmacy computer 770 is then used to perform the method of the present invention.

Similarly, the pharmacy computer 770 may optionally utilize a separate server 910 to perform some of the steps of the method of the present invention. By allocating a portion of the method of the present invention to the separate server 710, a pharmacist may capitalize upon economies of scale and gain additional speed and reduce processing time by employing a distributed computing scenario. For example, server 710 may populate the form with the appropriate fields to be completed by the pill-user with the pill user's computer 750a or with the pharmacy computer 770. Likewise, the pharmacy computer 770 may further distribute the steps of the present invention by separating the medication database 720 from the pharmacy computer and the server as well.

Using any of the computer system 700 scenarios and configurations, the pill-user completes the form. The needed information can be readily obtained from the current pill-bottle labels and existing prescriptions. The completed form lists all the pills taken daily by the individual, in time sequence. Pills taken only "as needed" are added to the end of the list and are designated as such. The list includes each pill's name, dosage, time taken, and general purpose of the medication. If necessary, the patient can get help from the prescribing doctor or nurse. Once the list of medications is specified, the pharmacist or aide transfers the list into the pill pack computer program. The pill pack computer program performs the method of the present invention by using the list of a pill-user's medications to determine the size and configuration of a pill pack container that will effectively and efficiently store and dispense a pill-user's medication over a predetermined period. The list of medications may be supplemented by a supplementary medication questionnaire to list medications that are taken concurrently in other forms, such as liquids, powders, inhalers, injections, or the like. These items are added to the list of (pill) medications in order to be checked for potential drug incompatibility. The pills to be taken are then incorporated into the pill pack computer program.

The pill pack computer program uses a database of brand-name and generic pills to categorize and configure the pill pack container. As the pill-user enters the specific pill information into the medication list, the computer program uses the pill pack database to automatically correct the medication name, dosage, and purpose in step 810. The pill pack database contains entries for existing medications and can be expanded with additional medications. Additionally, at step 815, the program determines the porthole size required for each pill's compartment port, for example, Closed (X), Small (7 mm), Medium (11 mm), or Large (15 mm), the details of which are described below. If an obscure medication is not found in the pill database, the user may perform a manual check to determine size and shape information and manually enter the data into the pill pack computer program.

In step 820, the computer program automatically adds the size of the compartment needed to store a supply of the pills for a predetermined time duration for each of the pill data listed on the questionnaire. For example, a basic 15 ml compartment stores about 35 relatively small pills, adequate for a typical one-a-day one-month supply. Larger pills need larger compartments, as well as larger porthole openings. If two or more pills need to be dispensed from the same compartment, or if more than a month's supply must be stored, the indicated compartment size can be increased by the pharmacist to allow for such variances. The pill pack computer program automatically organizes the pills in each time slot into the most efficient optional compartment size combinations based upon the number of pills and the size of each pill required for each time slot.

In step 825, the pill pack computer program totals the compartment sizes required for that pill-user, and in step 830 selects the next available pill pack container size having a larger capacity as the optimal size required. The pill pack computer program also automatically adds to the medication list the porthole opening size required for each pill, for example, Closed (X), Small (7 mm), Medium (11 mm) or Large (15 mm). The pill pack computer program may also automatically add a word or two regarding the general purpose of each pill, if the user did not provide an adequate description.

In step 832, the program determines the placement of the removable dividers and porthole inserts in the pill pack container. Pharmacy computer programs are used to check lists of medications for possible incompatibilities that might cause medical problems or contraindications. In step 835, the pill pack software interfaces with these programs and alerts the pharmacist of any possible contraindications or incompatibilities. Preferably, all the listed medications and supplementary medications are checked for incompatibilities automatically. If potential medical conflicts between any of the medications are identified in step 840, they should be discussed with the pill-user and the referring physician in step 845. Corrective substitutions or deletions should be made or other measures taken, as appropriate in step 850, before the pill list is finalized.

Optionally, the pharmacist may add the pharmacy number and refill date of each prescription pill to the medication list if not already provided by the user. The actual cost of the pills could also be included, if desired. Each pill name, dosage, purpose and related information derived from the questionnaire, pharmacist, or computer program, can be previewed on the monitor display. The pills are preferably grouped and sequenced based on the time of day they are to be taken. Within any single time slot the order of the pills may be rearranged by the pill pack computer program to optimize container space allocation. The final sequence is then approved on the computer by the pharmacist at step 855. In step 860, the computer program automatically assigns a series number to each pill compartment in the finalized list of medications. This also becomes the series number of that pill's storage compartment. If a pill is routinely taken more than once a day, the medication will receive more than one series number. The pills will then be dispensed in the proper order according to series number and time of day.

Any pill taken on an "as needed" basis is placed at the end of the series. The tray is rotated to that compartment's series number whenever the "as needed" pill is required. After taking the "as needed" pill, the tray is reset to its previous series number and time. If the user wishes to discontinue taking a certain pill, the corresponding pill pack compartment should be emptied. At the next refill, the matching line on the cover label is deleted, the compartment's lid label box marked X, and its porthole shut with a "Closed" port insert. Updated pill pack labels can be provided each month, or any other time period, as dispensed or required by the prescription.

The pill pack container is easily adaptable to a great variety of pill regimens. For example, in one implementation, the pill pack container allows storage of more than a one month's supply of pills to reduce the frequency of refills. One person may prefer a smaller pill pack with more frequent refills, another person may prefer a larger pill pack with fewer refills. Someone taking a large number of pills each day may choose to divide them between two pill packs, for example, by separating the AM pills from the PM pills, or by separating Short-term pills from Long-term pills.

Figure 9:
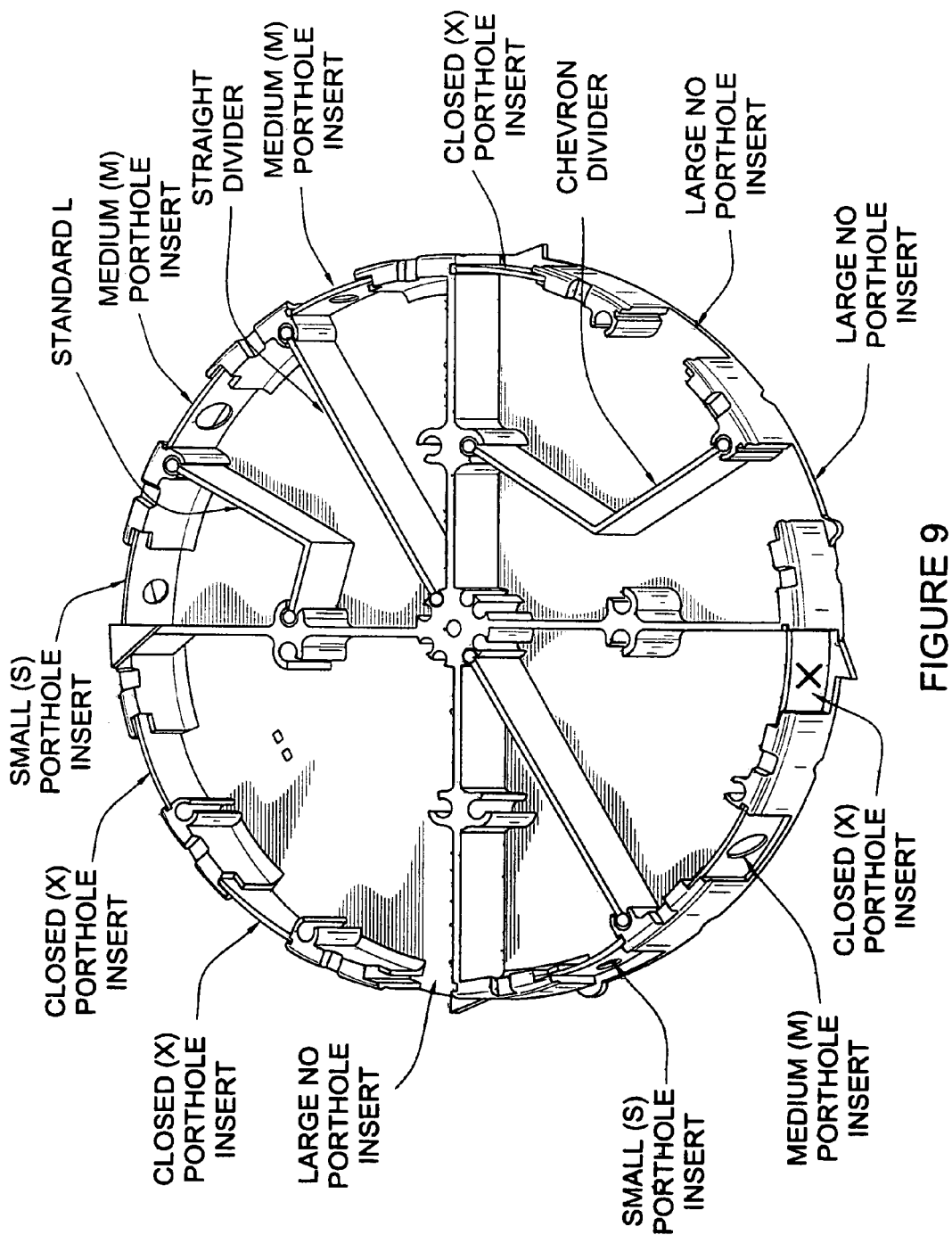
FIG. 9 illustrates an exemplary preparation diagram used to fill the pill pack container in accordance with one embodiment of the present invention.

When the pill list is finalized and displayed on the monitor, the pharmacist accepts the finalized list of medications in step 865. The pharmacist can use the computer to print out a preparation diagram in step 870. Of course, the pharmacist can merely view the preparation diagram and configure the pill pack accordingly. The preparation diagram indicates the required pill pack container size, the required size of each porthole, and exactly which of the removable divider walls must be removed or replaced. The preparation diagram identifies each compartment by its series number, or other manner, and shows its location, size and shape, as well as its pill name and dosage. The diagram is placed alongside the tray with their first compartments matching. An example of a preparation diagram is shown in FIG. 9.

Guided by the preparation diagram, in step 875 the pharmacist or assistant now inserts or removes standard-L and reversed-L divider walls to configure the container exactly as shown on the preparation diagram. The preparation diagram also identifies each porthole insert as Closed (X), Small (S), Medium (M), or Large (L). The pharmacist places X, S, or M porthole inserts into the vertical slots of each tray port opening as indicated in the preparation diagram. Portholes marked L receive no insert. Each large compartment with two or three portholes will have only the porthole used to dispense the pills fitted to the required size. All unused ports are marked X and are closed. The pharmacy receives each pill pack container 10 with an initial set of the most commonly used removable standard-L and reversed-L divider walls in their respective slots. Guided by the preparation diagram, the pharmacist removes any divider walls not required and replaces others with Standard-L, Reversed-L, Straight or chevron divider walls, exactly as shown in the preparation diagram. Unneeded dividers are returned to inventory. The tray now has correctly-sized compartments and portholes. The preparation sheet may now be discarded. At this point the pill pack container has been structurally tailored to the exact needs of its new patient owner. The process can be completed in a few minutes.

In step 880, the pharmacist prints out the computer-formatted pill pack labels, which may optionally be pre-cut to the shape of the cover. The pill pack labels may include a lid label 80, an example of which is shown in FIG. 5. The pill pack labels may also include a cover label 88, an example of which is shown in FIG. 6. The cover label 88 displays a detailed pill chart as shown in FIG. 6. The example cover label 88 may further include the series number of the medication, the time the medication is to be taken, the name and dose of the medication, a brief description of the purpose for which the medication is taken, as well as the patient's name, the name of the pharmacy, the name of the prescribing physician, the date and time that the prescription was filled, and dispensing information such as the prescription number and refill information. As noted above, an image of the pills may further be provided.

As shown in FIG. 5, the example lid label 80 may include window spaces 84 around the perimeter of the lid label 80 indicating each compartment's series number, time to administer the pill, and porthole opening information. An optional rear tray label (not shown) may further identify certain key people such as the pharmacist, the referring physicians, and the like.

In step 885, the pharmacist aligns and affixes the cover label 88 to the underside of the cover. By affixing the cover label 88 to the underside of the cover, the printed information on the cover label is visible through a transparent cover and remains protected from dirt and other elements that may soil an exposed cover label through routine handling. Alternatively, the cover label 88 may also be affixed to the top of a cover for improved access when protection from handling is not at issue. In any case, to affix the cover label 88, the pharmacist removes the round cover label 88 from its printed sheet. The cover label 88 has a pre-cut open window 86 at the top of the label 88. Double-stick tape tabs or other adhesives are placed under the top of the transparent cover 16 at inscribed locations. Using the printed label window 86 and "up" arrowhead 96, the label is aligned with the matching dispensing opening 18 and inscribed window 17 of the transparent cover 16. The rest of the cover label 88 is then lowered onto the adhesive tabs. The chart on the cover label 88 lists each pill by series number, time of day, name, dosage, and related information on separate lines.

Once the cover label 88 is affixed, the pharmacist removes, aligns, and affixes the lid label 80 in step 890. The pharmacist removes the lid label 80 from its sheet and attaches it on top of the lid 14 using adhesive tabs. In particular, double-adhesive tabs are attached on top of the lid 14 at inscribed sites. The lid label 80 is lowered onto the lid 14 so that its printed triangle 82 fits precisely over the cut-out triangle 72 on the edge of the lid 14. It is held there while the rest of the lid label 80 is pressed down onto the adhesive tabs. The lid label 80 is centered so that the printed window space 84 for each pill now matches their respective tray port openings 40 and displays the series number and time to take the pill. However, as noted, if a port has been closed, the lid label 80 has only an "X" printed in its window space 83.

As shown in FIG. 5, lid label 80 features additional information and alignment tools. For example, a thin horizontal line and a center dot 81 mark the bottom edge of each window space 84 to indicate its position in the cover window 86 of the cover label 88. A "down" arrowhead 79 appears on the center line of the interspace between any two window spaces. The down arrowhead 79 will line up with an "up" arrowhead 96 on the cover label 88 to form an X. This is useful when positioning the tray to activate a sliding pin-lock (not shown) on the rim of the cover. A red "STOP" warning 85 is also printed on the lid label 80 in the interspace between the last window space of each time slot and the first window space of the next time slot. The time for the next pill is also printed in this space to inform the user.

In steps 891 and 892, the pharmacist can use an optional triangular rear tray label (not shown) which may also be printed. The optional rear tray label attaches to the underside of the tray 12 in the angle formed by the lower two rotation bars 62 using small adhesive tabs or other adhesive. The rear label may further identify the pill-user, the pharmacist, or the physician(s), and it may display a bar-code corresponding to the pill-user.

In step 895, the pharmacist loads the pills into each of their serially numbered compartments. An elastic loading band may optionally be employed to seal all open port-holes while loading pills. Once the compartments are loaded with the desired pills in their respective compartments, the pharmacist places the lid 14 on top of the tray 12 in step 897. The printed and cut-out triangles on the edge of the lid 14 fit over the triangular projection 74 on the outer edge of the tray 12. The lid sidewall segments 68 and stabilizer ring 76 secure all the port inserts 44 and non-planar removable dividers 28 in their assigned locations in the tray 12.

In step 899, the pharmacist aligns the cover side rails 92 over the first compartment of the tray 12, slides the pin-lock into its "open" position, and press-locks the cover 16 over the loaded tray 12 and lid 14, proceeding clockwise. This forces the rotation ridge segments 50 on the cover 16 into the tray groove 48 and locks the cover 16 onto the tray 12 but allows the tray 12 to rotate relative to the cover 16. The pill pack container is now ready for use and transfer to its new owner.

Refills and changes to a pill-user's medication regimen may also be facilitated by using the pill pack container of the present invention. The pharmacy and the pill-user would benefit whenever two or more prescription refills that happen to occur on different days of the month could be synchronized. Synchronizing refill dates would require the cooperation of the pill-user's HMO or other third-party payer who may also benefit from the reduced number of pharmacy interactions. Permission to add additional pills to the number prescribed for the first refill only, or to reduce that number in some cases, would be desirable to ensure that all subsequent refill dates occur on the same convenient day of the month for that particular pill-user.

The method of the present invention may be modified to synchronize multiple prescriptions to provide a single starting and stopping date. The pill pack computer program can then calculate the pill pack container requirements based on the new number of pills. Similarly, additional computer processes may be employed to allow the pill-user to provide prior notification to the pharmacy with regard to the pill-user's pill pack requirements. The pill-user can send an electronic mail message or otherwise provide written or oral notice to the pharmacy that the pill-user requires a refill or a change in medication regimen. Similarly, a refill schedule may also be used where refills are automatically generated and filled by the pharmacist periodically as dictated by the pill-user, referring physicians, and/or the pharmacist. The computer processes of the present invention may also be used by the pharmacy to initiate refill inquiries to the pill-user if the pill-user has not notified the pharmacy regarding refills after a predetermined time period expires.

By using these additional computer processes, refill pill pack containers may be prepared ahead of the pill-user's arrival at the pharmacy to save time. When the pill-user arrives, the pharmacist may simply scan the bar-code on the pill-user's in-use pill pack container to identify the pill-user and to display all the current pill information on a computer monitor. Any necessary additions, deletions or other changes may then be entered. Updated labels can be rapidly printed to replace the existing labels.

A new pill pack container may occasionally be required if a medication regimen change demands a different number, size, or sequence of pills, thereby dictating a new number or configuration of pill compartments. The new pill pack container is prepared by following the preparation instructions for the new medication regimen in a manner similar to that described above.

To further save time and to capitalize on economies of scale, an HMO or other prescription drug plan may periodically fill and dispense recurring prescriptions by mail or by a similar delivery service. These entities may be visualized as prescription-filling warehouses that receive prescription requests from pill-users, and then fill the medication order by filling the prescription and delivering it to the proper pill-users. The pill pack system and method can be effectively adapted to the increasingly popular, cost-effective, and convenient purchase of pill medications from mail-order or on-line pharmacies. These purchasers tend to be long-term multiple prescription pill-users. Face-to-face interactions with the pharmacist are replaced by telephonic, fax and e-mail communications.

To provide even greater flexibility in filling prescriptions using the pill pack system and method of the present invention, pharmacies may solicit information from pill-users with regard to additional medications taken that are also available in pill form, but are purchased by the pill-user in a different form. These pills may include over-the-counter medications or other prescription medications that the pill-user chooses not to purchase from the pharmacy or medication-supplier employing the pill pack system of the present invention. The pill pack questionnaire may invite listing all the additional medications the pill-user normally purchases elsewhere. In return the company or pharmacy could prepare a customized pill pack container with additional empty compartments for all the extra pills with their correct compartment configuration and porthole sizes. Each month the pill pack cover label would then display the pills provided by the pill-pack-container-supplying pharmacy as well as the extra pills denoted in a different fashion, such as listed in a different font or color, or some other distinguishing manner. The mail-order pill-pack-container-supplying pharmacy pills would be preloaded in the pill pack container. The pill-user would load the extra pills into their pre-labeled pill pack compartments, for example, using a pill refill-tray accessory. Empty containers may be simply discarded.

An added benefit is that the mail-order, Internet, or neighborhood pharmacist can detect potential drug incompatibilities with all medications that the pill-user plans to use by broadening the incompatibility check to evaluate a wider range of medications. As before, the incompatibility check may prevent adverse interactions by interfacing the pill pack computer software with a medication incompatibility program. Thus, the mail-order user would receive the same expanded professional oversight provided by a local pharmacist, in addition to the unified pill organization, storage and dispensing features possible with the pill pack system and method of the present invention. This additional service may provide the additional benefit to the pharmacy by encouraging the pill-user to make future purchases of those "extra" pills directly from the mail-order, Internet, or neighborhood pharmacy, using the pill pack system and method of the present invention.

Once configured and filled, the pharmacist supplies the pill pack container to its new owner, and ensures that the pill pack container is tailored to the new owner's specific needs. This restores the role of the pharmacist as the primary advisor to patients for all the medications or pills taken at home for a great variety of ailments and health concerns.

The pill pack system may be implemented by a general purpose computer programmed to accomplish the disclosed functions. Accordingly, the functions described herein may be implemented as computer hardware and/or computer software. Various devices may be used to provide the computer or computer system for effecting the invention. For example, the above-described devices and subsystems of the exemplary embodiments of FIG. 7 can include, for example, any suitable servers, workstations, PCs, laptop computers, PDAs, Internet appliances, handheld devices, cellular telephones, wireless devices, other devices, and the like, capable of performing the processes of the exemplary embodiments of FIG. 7.

The devices and subsystems of the exemplary embodiments can communicate, for example, over a communications network, and can include any suitable servers, workstations, personal computers (PCs), laptop computers, PDAs, Internet appliances, set top boxes, modems, handheld devices, telephones, cellular telephones, wireless devices, other devices, and the like, capable of performing the processes of the disclosed exemplary embodiments. The devices and subsystems, for example, can communicate with each other using any suitable protocol and can be implemented using a general-purpose computer system, and the like. One or more interface mechanisms can be employed, for example, including Internet access, telecommunications in any suitable form, such as voice, modem, and the like, wireless communications media, and the like. Accordingly, communications networks employed can include, for example, wireless communications networks, cellular communications networks, satellite communications networks, Public Switched Telephone Networks (PSTNs), Packet Data Networks (PDNs), the Internet, intranets, hybrid communications networks, combinations thereof, and the like. In addition, the communications networks employed can be the same or different networks.

As noted above, it is to be understood that the exemplary embodiments are for representative purposes, as many variations of the specific hardware used to implement the disclosed preferred embodiments are possible. For example, the functionality of the devices and the subsystems of the exemplary systems can be implemented via one or more programmed computer systems or devices. To implement such variations as well as other variations, one or more computer system can be programmed to perform the special purpose functions of one or more of the devices and subsystems of the exemplary systems. In addition, associated data and information may be stored in one or more memories, such as a hard disk, optical disk, magneto-optical disk, RAM, and the like, and be implemented with one or more databases that can be organized using data structures, such as records, tables, arrays, fields, graphs, trees, lists, and the like.

All or a portion of the exemplary embodiments can be conveniently implemented using one or more general-purpose computer-systems, microprocessors, digital signal processors, micro-controllers, and the like. Appropriate software can be readily prepared by programmers of ordinary skill based on the teachings of the disclosed exemplary embodiments. In addition, the exemplary systems can be implemented by the preparation of application-specific integrated circuits or by interconnecting an appropriate network of component circuits.

While the present invention has been described in connection with a number of exemplary embodiments and implementations, the present invention is not so limited but rather covers various modifications and equivalent arrangements.

The invention claimed is:

1. A customizable medication storage and dispensing container for storing and dispensing medication comprising:
   a tray having a plurality of size-adjustable compartments, the compartments defined at least partially by a bottom wall, a peripheral wall, and a non-planar wall;
   a cover having at least one dispensing opening thereon, the cover being rotatably secured to the tray to allow selection of at least one of the plurality of size-adjustable compartments for dispensing of medication stored therein; and
   a plurality of port inserts for insertion in a port opening on the peripheral wall of the tray;
   wherein the tray further includes a plurality of tray rim segments extending vertically upward from the bottom wall to form the tray peripheral wall, the plurality of tray rim segments at least partially defining the port opening from which medication is accessible; and
   wherein at least one of the plurality of port inserts includes a porthole opening thereon.

2. The customizable medication storage and dispensing container of claim 1, wherein the porthole openings vary in size to aid in dispensing of medication having varying sizes and shapes.

3. A customizable medication storage and dispensing container for storing and dispensing medication comprising:
   a tray having a plurality of size-adjustable compartments, the compartments defined at least partially by a bottom wall, a radial wall, and a peripheral wall, the tray including a port opening on the peripheral wall of the tray and a port insert for insertion in the port opening from which medication is accessible; and a cover having at least one dispensing opening thereon, the cover being rotatably secured to the tray to allow selection of at least one of the plurality of size-adjustable compartments for dispensing of medication stored therein;

wherein at least one of the plurality of port inserts includes a porthole opening thereon.

4. The customizable medication storage and dispensing container of claim 3, wherein the porthole openings vary in size to aid in dispensing of medication having varying sizes and shapes.

5. A customizable medication storage and dispensing container for storing and dispensing medication comprising:

a tray having a plurality of size-adjustable compartments, the compartments defined at least partially by a bottom wall, a radial wall, and a peripheral wall, the tray including a port opening on the peripheral wall of the tray and a port insert for insertion in the port opening from which medication is accessible; and a cover having at least one dispensing opening thereon, the cover being rotatably secured to the tray to allow selection of at least one of the plurality of size-adjustable compartments for dispensing of medication stored therein;

wherein the port insert includes a porthole opening thereon; and wherein the tray further includes a removable non-planar wall; and wherein the removable non-planar wall has one of an L shape, a reverse-L shape, or a chevron shape.

* * * * *